United States Patent
Papay et al.

(10) Patent No.: US 10,052,186 B2
(45) Date of Patent: Aug. 21, 2018

(54) PROSTHETIC IMPLANTS

(71) Applicants: THE CLEVELAND CLINIC FOUNDATION, Cleveland, OH (US); OsteoSymbionics LLC, Cleveland, OH (US)

(72) Inventors: Francis A. Papay, Westlake, OH (US); Jessie San, Cleveland, OH (US); Nicholas T. Wilkins, Streetsboro, OH (US); Cameron J. Fordyce, Bay Village, OH (US)

(73) Assignees: OSTEOSYMBIONICS LLC, Cleveland, OH (US); THE CLEVELAND CLINIC FOUNDATION, Cleveland, OH (US)

( * ) Notice: Subject to any disclaimer, the term of this patent is extended or adjusted under 35 U.S.C. 154(b) by 268 days.

(21) Appl. No.: 14/510,541

(22) Filed: Oct. 9, 2014

(65) Prior Publication Data
US 2015/0105858 A1     Apr. 16, 2015

Related U.S. Application Data

(60) Provisional application No. 61/889,218, filed on Oct. 10, 2013, provisional application No. 62/028,343, filed on Jul. 24, 2014.

(51) Int. Cl.
*A61F 2/02* (2006.01)
*A61L 27/18* (2006.01)
(Continued)

(52) U.S. Cl.
CPC .............. *A61F 2/02* (2013.01); *A61F 2/0059* (2013.01); *A61F 2/2875* (2013.01); *A61L 27/18* (2013.01);
(Continued)

(58) Field of Classification Search
CPC ...... A61F 2/186; A61F 2/2875; A61F 2/0059; A61F 2002/2878; A61F 2250/0036;
(Continued)

(56) References Cited

U.S. PATENT DOCUMENTS

| | | |
|---|---|---|
| 5,514,179 A | 5/1996 | Brennan |
| 6,277,150 B1 | 8/2001 | Crawley et al. |

(Continued)

FOREIGN PATENT DOCUMENTS

| | | | | |
|---|---|---|---|---|
| FR | 2447182 A1 | * | 8/1980 | ........... A61F 2/0059 |
| FR | 2447182 A1 | * | 8/1980 | ............... A61F 1/00 |
| WO | 2012105736 A1 | | 8/2012 | |

OTHER PUBLICATIONS

Pegram, Trey A. et al., "Effects of Porous Silicone Implant Onlays on the Mandible of the New Zealand White Rabbit", pp. 1-18.
(Continued)

*Primary Examiner* — Christopher D Prone
*Assistant Examiner* — Rokhaya Diop
(74) *Attorney, Agent, or Firm* — Tarolli, Sundheim, Covell & Tummino LLP

(57) ABSTRACT

A prosthetic implant includes an anterior surface, configured for at least partial contact with an underside of a patient's facial soft tissue. A posterior surface is oppositely placed to the anterior surface. The posterior surface is configured for at least partial contact with a patient's facial bony tissue when the anterior surface is in at least partial contact with the patient's facial soft tissue. An implant body is defined by the anterior and posterior surfaces and extends transversely therebetween. A selected portion of the posterior surface has a texture that mechanically differs from a texture of a majority of the anterior surface.

15 Claims, 18 Drawing Sheets

(51) Int. Cl.
   *A61F 2/00*      (2006.01)
   *A61F 2/18*      (2006.01)
   *A61F 2/28*      (2006.01)
   *A61F 2/30*      (2006.01)
(52) U.S. Cl.
   CPC ....... *A61F 2/186* (2013.01); *A61F 2002/2807* (2013.01); *A61F 2002/2878* (2013.01); *A61F 2002/2882* (2013.01); *A61F 2002/2885* (2013.01); *A61F 2002/2889* (2013.01); *A61F 2002/30011* (2013.01); *A61F 2002/30013* (2013.01); *A61F 2002/30069* (2013.01); *A61F 2002/30131* (2013.01); *A61F 2002/30932* (2013.01); *A61F 2220/0033* (2013.01); *A61F 2230/0013* (2013.01); *A61F 2250/0023* (2013.01); *A61F 2250/0024* (2013.01); *A61F 2250/0036* (2013.01); *A61F 2250/0058* (2013.01); *A61F 2250/0062* (2013.01)
(58) Field of Classification Search
   CPC .............. A61F 2002/30131; A61F 2/02; A61F 2002/2889; A61F 2002/2882; A61F 2002/2885; A61F 2220/0033; A61F 2230/0013; A61F 2250/0058; A61F 2002/2807; A61F 2002/30011; A61F 2002/30013; A61F 2002/30069; A61F 2250/0023; A61F 2250/0062; A61L 27/18
   See application file for complete search history.

(56) References Cited

U.S. PATENT DOCUMENTS

2009/0198335 A1* 8/2009 Barbosa ................ A61F 2/0059
                                                          623/11.11
2012/0330427 A1* 12/2012 Yaremchuk ........... A61F 2/0059
                                                          623/17.18

OTHER PUBLICATIONS

PCT International Search Report and Written Opinion for PCT/US2014/059861, dated Jan. 28, 2015, pp. 1-14.

* cited by examiner

PROSTHETIC IMPLANTS

RELATED APPLICATION

This application claims priority from U.S. Provisional Application No. 61/889,218, filed 10 Oct. 2013, and from U.S. Provisional Application No. 62/028,343, filed 24 Jul. 2014, the subject matter of both of which is incorporated herein by reference in its entirety.

TECHNICAL FIELD

This disclosure relates to an apparatus and method for use of a prosthetic implant and, more particularly, to a method for use and apparatus of a prosthetic implant that can be used in reconstructive and/or cosmetic surgery, particularly of the head and/or face.

BACKGROUND

A prosthetic implant can be used in reconstructive and/or cosmetic surgery, such as of the head and/or face—for example, a prosthetic orbital implant could be used as a rejuvenating reconstructive solution/treatment for patients who have experienced bone resorption of the orbital rim and herniation of the orbital septum through aging and gravity. Currently, such condition(s) are corrected, for cosmetic or therapeutic reasons, via fat or Botox injections and/or traditional Lower Blepharoplasty procedures.

The Lower Blepharoplasty procedure currently used reduces excess skin, smoothes the underlying musculature, tightens the supporting structures, and resects or redrapes excess fat to smooth the transition from lower eyelid to the cheek.

In addition to the described orbital use, patients may have desire therapeutic and/or cosmetic treatment of chin, malar (cheek or side of the head), mandible, maxilla, and/or nasal conditions.

SUMMARY

A prosthetic implant includes an anterior surface, configured for at least partial contact with an underside of a patient's facial soft tissue. A posterior surface is oppositely placed to the anterior surface. The posterior surface is configured for at least partial contact with a patient's facial bony tissue when the anterior surface is in at least partial contact with the patient's facial soft tissue. An implant body is defined by the anterior and posterior surfaces and extends transversely therebetween. A selected portion of the posterior surface has a texture that mechanically differs from a texture of a majority of the anterior surface.

A method of using a prosthetic implant for a patient having bony tissue and soft tissue includes providing a prosthetic implant. The prosthetic implant includes an anterior surface, configured for at least partial contact with an underside of a patient's facial soft tissue. A posterior surface is oppositely placed to the anterior surface. The posterior surface is configured for at least partial contact with a patient's facial bony tissue when the anterior surface is in at least partial contact with the patient's facial soft tissue. An implant body is defined by the anterior and posterior surfaces and extends transversely therebetween. A selected portion of the posterior surface has a texture that mechanically differs from a texture of a majority of the anterior surface. A predetermined implant site is surgically exposed. The prosthetic implant is placed into a predetermined implantation relationship with the implant site. The prosthetic implant is secured in the implantation relationship. The implant site and prosthetic implant are surgically covered.

BRIEF DESCRIPTION OF THE DRAWINGS

Reference may be made to the accompanying drawings, in which.

DESCRIPTION OF ASPECTS OF THE DISCLOSURE

The invention comprises, consists of, or consists essentially of the following features, in any combination.

Figure 1:
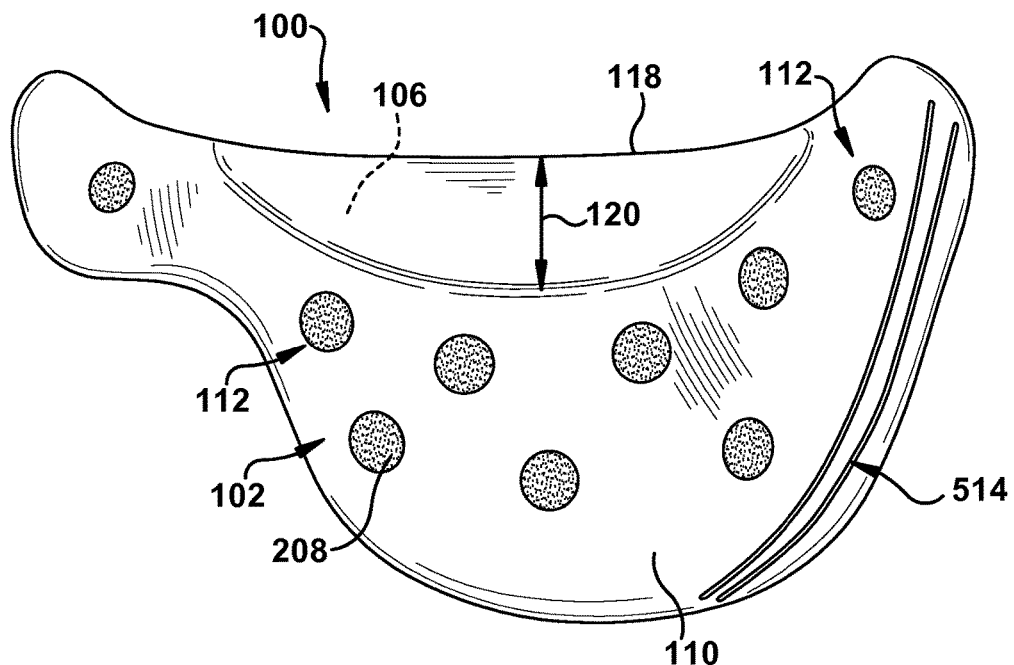
FIG. 1 is an anterior view of an example construct according to the present invention.

FIG. 1 depicts an example prosthetic implant 100 according to an aspect of the present invention, which can be used in addition to, or instead of, fat or Botox injections and/or traditional/known plastic/cosmetic surgical procedures, for purposes of cosmetic and/or reconstructive (of a congenital or acquired defect) surgeries. The prosthetic implant 100 is shown in FIG. 1 and described herein as a prosthetic orbital implant, for use in, for example, a Lower Blepharoplasty procedure for surgical correction of a herniated orbital septum and/or resorbed orbital rim. The prosthetic implant 100 shown in FIG. 1 may at least reduce, if not eliminate, the need for a traditional Lower Blepharoplasty procedure. Traditional Blepharoplasty will treat the symptoms of aging periorbita temporarily, while the prosthetic implant 100 is a lasting solution that helps correct the effects of gravity and time.

The prosthetic implant 100 may help provide a permanent solution to eliminate bags under the eye (one of the symptoms of aging periorbita) and augment a previously resorbed orbital rim. The prosthetic implant 100 can help provide patients with a more youthful appearance. Various prosthetic implants, such as the various constructs of the present invention shown and described herein, also or instead may help augment the orbital, malar, nasal, chin, mandibular, or maxillar region(s), and/or may be used as a midface augmentation. For example, the prosthetic implant 100 could be a prosthetic chin implant, a prosthetic malar implant, a prosthetic orbital implant, a prosthetic nasal implant, and/or a prosthetic implant for use in conjunction with any portion of a patient's anatomy, and for any desired reason.

A prosthetic implant according to the present invention may be patient-specific or a stock item, and, particularly in the latter case, may be available in left/right versions and/or a range of desired sizes/dimensions. Suitable materials for at least a portion of the prosthetic implant include, but are not limited to, one or more of Poly(methyl methacrylate) (PMMA); Polyether ether ketone (PEEK); Polytetrafluoroethylene (PTFE); expanded polytetrafluoroethylene (ePTFE); Polylactic acid (PLA); Polycaprolactone (PCL); and silicone elastomers. It is generally contemplated that the prosthetic implant will be generally rubbery and flexible for most use environments of the present invention, but at least a portion of the prosthetic implant may be relatively rigid or inflexible as compared to at least a portion of the rest of the prosthetic implant. Any suitable manufacturing process, including, but not limited to, molding and additive manufacturing processes, may be used to create a custom or stock prosthetic implant according to the present invention.

Returning to FIGS. 1-2, it can be seen that the depicted prosthetic implant 100 includes an anterior surface 102, which is configured for at least partial contact with an underside of a patient's facial soft tissue. A posterior surface 204 of the prosthetic implant 100 is oppositely placed to the anterior surface 102. The posterior surface 204 is configured for at least partial contact with a patient's facial bony tissue when the anterior surface 102 is in at least partial contact with the patient's facial soft tissue.

An implant body 106 is defined by the anterior and posterior surfaces 102, 204 and extends transversely therebetween. That is, the implant body 106 forms the "thickness" of the prosthetic implant 100. The implant body 106 is bounded by the anterior and posterior surfaces 102, 204, which meet at their respective outermost perimeters/edges to define the edges of the prosthetic implant 100.

Figure 2:
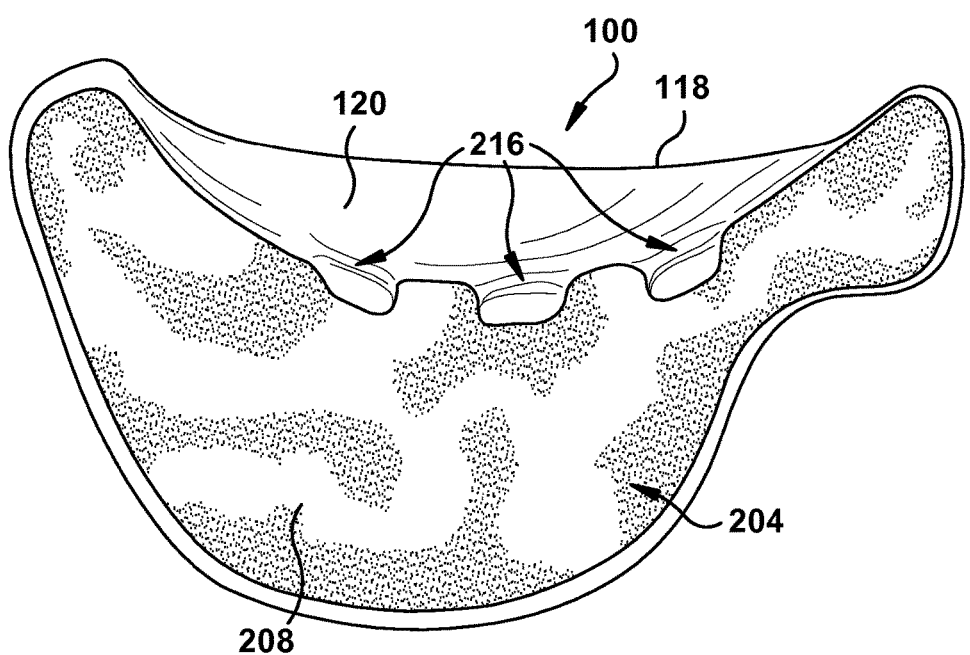
FIG. 2 is a posterior view of the construct of FIG. 1.
Figure 3:
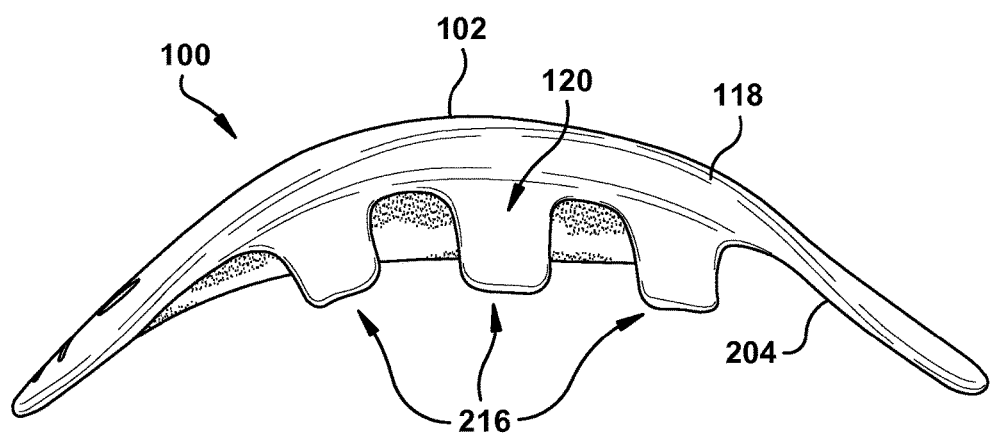
FIG. 3 is a superior view of the construct of FIG. 1.
Figure 4:
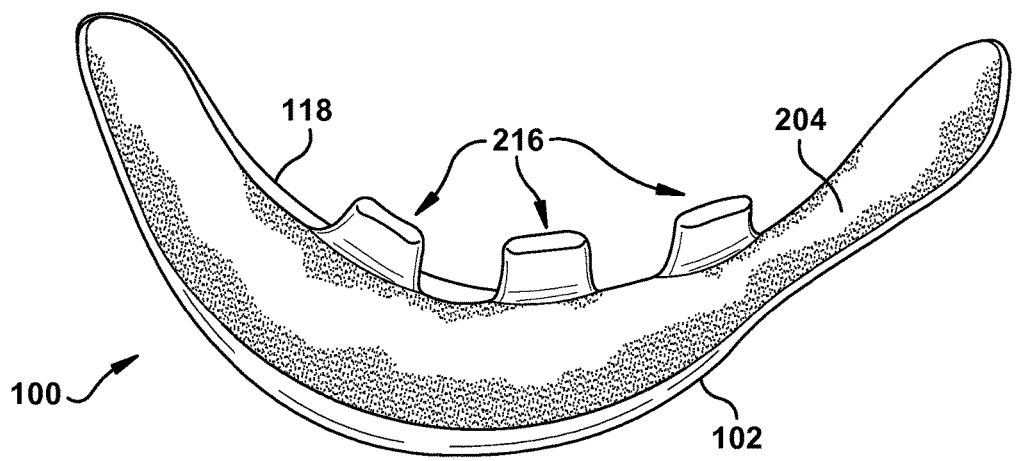
FIG. 4 is an inferior view of the construct of FIG. 1.

A selected portion, such as a supermajority, of the posterior surface 204 may have a texture that mechanically differs from a texture of a majority of the anterior surface 102. (The term "supermajority" is used herein to indicate a majority which is significantly larger than a simple majority.) The posterior surface 204 of the prosthetic implant 100, for example, may contain porous silicone 208, which sits in situ against the patient's bony tissue to help facilitate bone ingrowth and integration with the prosthetic implant 100, as well as to help prevent bone erosion. This configuration is shown in FIG. 2. Porous silicone 208 is absorbent, which may allow, when present, for infusion of the prosthetic implant 100 before or during implantation with pharmaceuticals and/or growth-inducing agents, such as, but not limited to, hyaluronic acid, growth hormone, antibiotics, silver or other metals, or any other desired "doping agent". The intricate surface "micro-texture" of the porous silicone 208 material exposed to patient tissue and the resultant ingrowth of patient tissue into the prosthetic implant 100 can also help prevent capsular contraction.

The anterior surface 102 of the prosthetic implant 100, shown in FIG. 1, may be, for example, solid silicone 110. As such, a majority of the anterior surface 102 shown is substantially smooth and thus mechanically differs from a supermajority of the posterior surface 204 of the construct depicted in FIGS. 1-2. However, as can be seen in these Figures, the anterior surface 102 includes a "macro-texture" with a plurality of apertures 112 extending at least partially into the implant body 106. Optionally, at least one aperture 112 may extend entirely through the implant body 106 transversely between the anterior and posterior surfaces 102, 204 for fluid communication therebetween. When present, one or more of the apertures 112 may contain porous silicone 208 to promote muscle and tissue ingrowth and integration of the prosthetic implant 100 with the surrounding patient anatomy (via both "macro" ingrowth into the apertures 112 and "micro" ingrowth into the exposed porous silicone 208).

Stated differently, the prosthetic implant 100 may include a relatively solid/smooth-faced (described herein as "solid"), and optionally at least partially flexible surface (e.g., a chosen one of the anterior and posterior surfaces 102, 204), and a relatively porous surface (e.g., the other one of the anterior and posterior surfaces 102, 204), optionally of the same and/or a different material, attached to the solid surface and having a different surface texture than the solid surface. When present, the solid surface may help provide a mechanically supportive framework for the porous surface, particularly if the material of the porous surface is more flexible than the material of the solid surface. The anterior surface 102 and/or the posterior surface 204 may have any desired percentage, type, configuration, or other arrangement of micro-textured and/or macro-textured areas.

For example, both the posterior and anterior surfaces 204 and 102 may be made entirely of porous silicone 208. As another example, both the posterior and anterior surfaces 204 and 102 may be made entirely of solid silicone 110. As another example, a selected one of the posterior and anterior surfaces 204, 102 may be made entirely of porous silicone 208 and another one of the posterior and anterior surfaces 204, 102 may be made entirely of solid silicone 110. In addition to the porous silicone 208 and/or solid silicone 110 nature of the posterior and anterior surfaces 204 and 102, each of these surfaces may include micro-textures (e.g., the aforementioned porous silicone 208, a small-scale surface-roughened area, embedded grit/particles, or any other suitable surface treatment or combination thereof) and/or macro-textures (e.g., one or more of the aforementioned apertures 112 of any configuration, a grid or mesh overlay, a large-scale surface-roughened area, or any other suitable surface treatment or combination thereof), as desired for a particular use environment for the prosthetic implant. The term "micro-texture" is used herein mainly to indicate an interconnected, non-continuously-solid pore structure within a material, while a "macro-texture" will generally refer to an overlay or molded-in feature on the contour or surface of a structure. It is contemplated that any suitable surface treatment, whether applied directly to the material of the anterior or posterior surfaces 102, 204, or provided by a separate component attached to that material, could be used that provides desired mechanical properties to the various components of constructs according to the present invention, whether or not specifically shown and/or described herein.

Turning once again to the apertures 112, any desired number, placement, configuration, type, size, and/or shape of apertures 112 could be provided, as desired, to the posterior and/or anterior surfaces 204 and 102 of the prosthetic implant. As shown in FIGS. 1-2, at least one aperture 112 (here, all apertures 112 of the anterior surface 102) may contain a material (here, porous silicone 208) having a texture that mechanically differs from a texture of a majority of a chosen one of the anterior surface and the posterior surface 102 and 204. That is, the apertures 112 of the anterior surface 102 may include a filler material that is different from the material of the anterior and/or posterior surfaces 102, 204. Here, the apertures 112 are filled with porous silicone 208 (as a filler material), and the majority of the posterior surface 204 is porous silicone 208. Therefore, the (filler) material contained in at least one aperture 112 has a texture that is substantially the same as the texture of the majority of the posterior surface 204. Accordingly, the prosthetic implant 100 of FIGS. 1-2 could be produced, for example, by overmolding a solid silicone 110 subassembly including the anterior surface 102 with a porous silicone 208 subassembly including the posterior surface 204. Additive manufacturing is also a possible manufacturing technique for at least part of the prosthetic implant 100. It is contemplated, however, that one or more apertures 112 could be filled with a filler material, provided in any suitable manner, that differs from a material of the anterior and/or posterior surfaces 102, 204 and/or from a filler material of one or more other apertures 112. One of ordinary skill in the art will be able to choose and configure any suitable textures and/or materials for part or all of the prosthetic implant 100 for a particular use environment.

As shown in FIG. 2, at least one tab 216 can be provided, such as the three tabs 216 shown protruding transversely from at least a portion of the posterior surface 204. The at least one tab 216, when present, is configured for engagement with at least a portion of the patient's bony tissue, as will be discussed in detail below. For example, when the prosthetic implant 100 is a prosthetic orbital implant, the tab(s) 216 may rest on the orbital rim to help guide implantation and/or stabilize the implant post-operatively. In some use environments of the prosthetic implant, the tab(s) 216, when present, may be used to mechanically secure the prosthetic implant 100 to adjacent patient tissue as desired—and/or the prosthetic implant 100 could itself be secured directly to the patient tissue as desired—optionally with the aid of sutures, adhesive, screws, or any other suitable attachment schemes.

An upper rim 118 may be formed by the implant body 106 at an uppermost (in the orientation of FIGS. 1-2) portion of the prosthetic implant 100 where the anterior and posterior surfaces 102 and 204 intersect. Optionally, a portion of the prosthetic implant 100 located directly beneath and adjacent to the upper rim 118 bulges anteriorly to create a protruding dam 120. That is, for some use environments, the dam 129 may extend superiorly (upward) and anteriorly from an area of the implant body 106 which substantially coincides with a vertical (in the orientation of FIG. 2) location of the tabs 216 on the implant body 106. In this example, the implant body 106 may bulge anteriorly, via the presence of the dam 120, to match, mirror, mimic, or otherwise echo or evoke the contour of a normal orbital/maxillary anatomy and to create an aesthetically pleasing transition between the prosthetic implant 100 and the patient's bone. The dam 120 of the prosthetic implant 100 may be located on an uppermost portion of the prosthetic implant 100 (when the patient is standing/sitting upright). For example, when the prosthetic implant 100 is a prosthetic orbital implant, the dam 120 may rest against the orbital septum to apply constant pressure and support. The dam 120 may be manufactured in solid silicone 110 and could be created during manufacture of the prosthetic implant 100 and/or could be added at some time between manufacture and implantation. The dam 120, when present, may utilize encapsulation of solid silicone 110 to further add volume to the orbital rim. The dam 120 may be used to help prop up the lower eyelid and/or prevent later sagging of the septum. The dam 120 may include and/or be adjacent to one or more tabs 216, of any desired configuration. For example, at least one tab 216 could be configured for engagement with at least a portion of the patient's bony tissue, and the dam 120 could then extend longitudinally between the upper rim 118 and the at least one tab 216.

Figure 5:
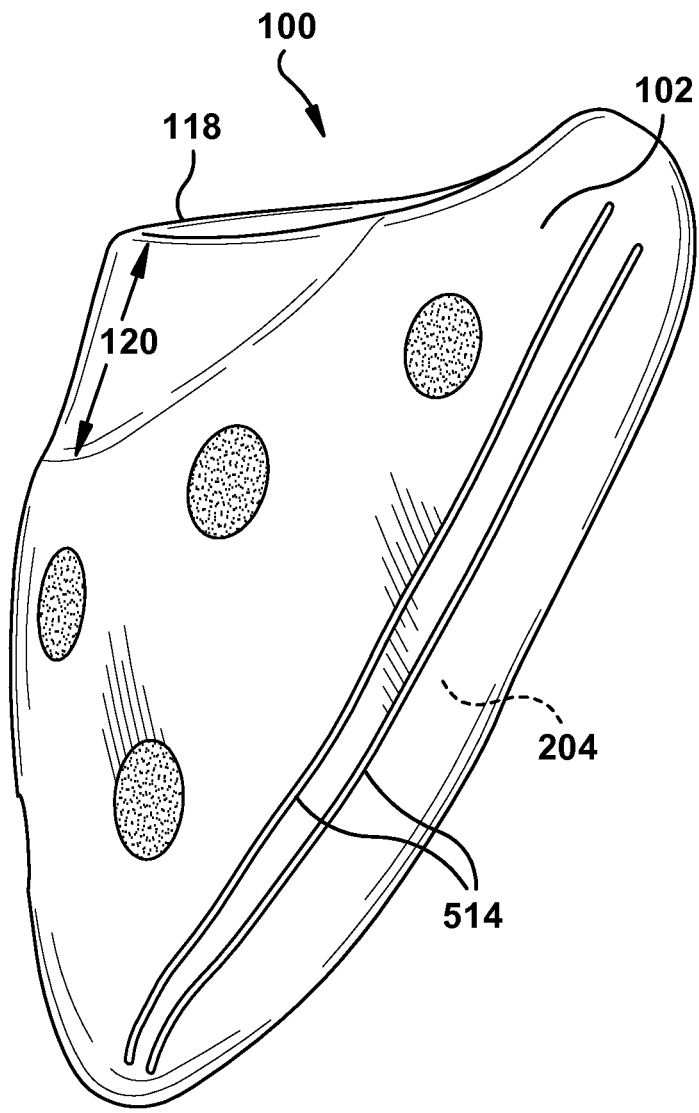
FIG. 5 is a partial lateral view of the construct of FIG. 1.

Optionally, and as shown in FIG. 5, one or more trim lines 514 could be provided, on any part of the prosthetic implant 100, to guide a user in cutting or otherwise machining away a portion of the implant body 106 as desired for a particular use environment. The trim lines 514, when present, could be patient-specific or stock, and could be two-dimensional (e.g., printed on the surface of the prosthetic implant 100) and/or three-dimensional (e.g., molded or otherwise recessed into or protruding above an immediately adjacent portion of the prosthetic implant 100). The trim lines 514 could be created during manufacture of the prosthetic implant 100 and/or could be added at some time between manufacture and implantation.

Figure 6:
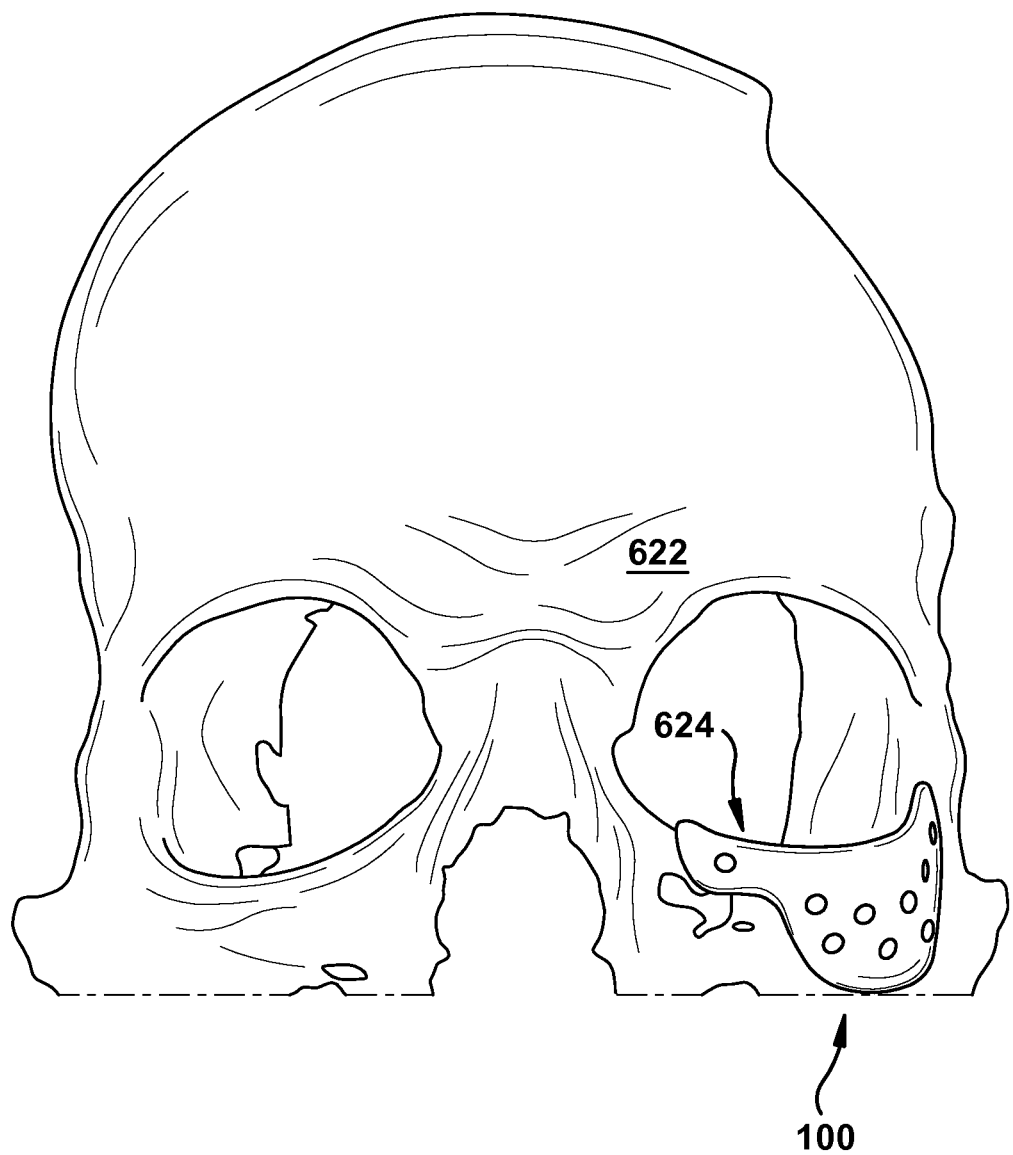
FIG. 6 is an anterior view of the construct of FIG. 1 in an example use environment.
Figure 7:
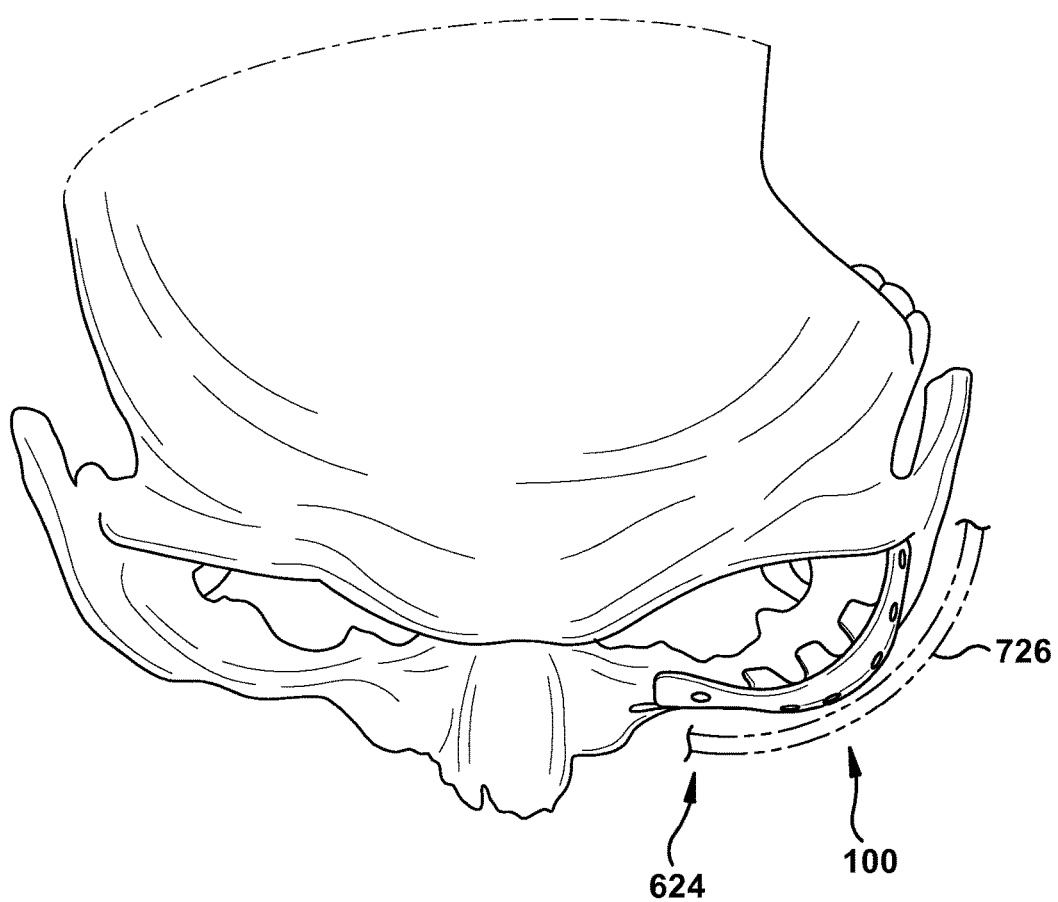
FIG. 7 is a superior view of the construct of FIG. 1 in an example use environment.
Figure 8:
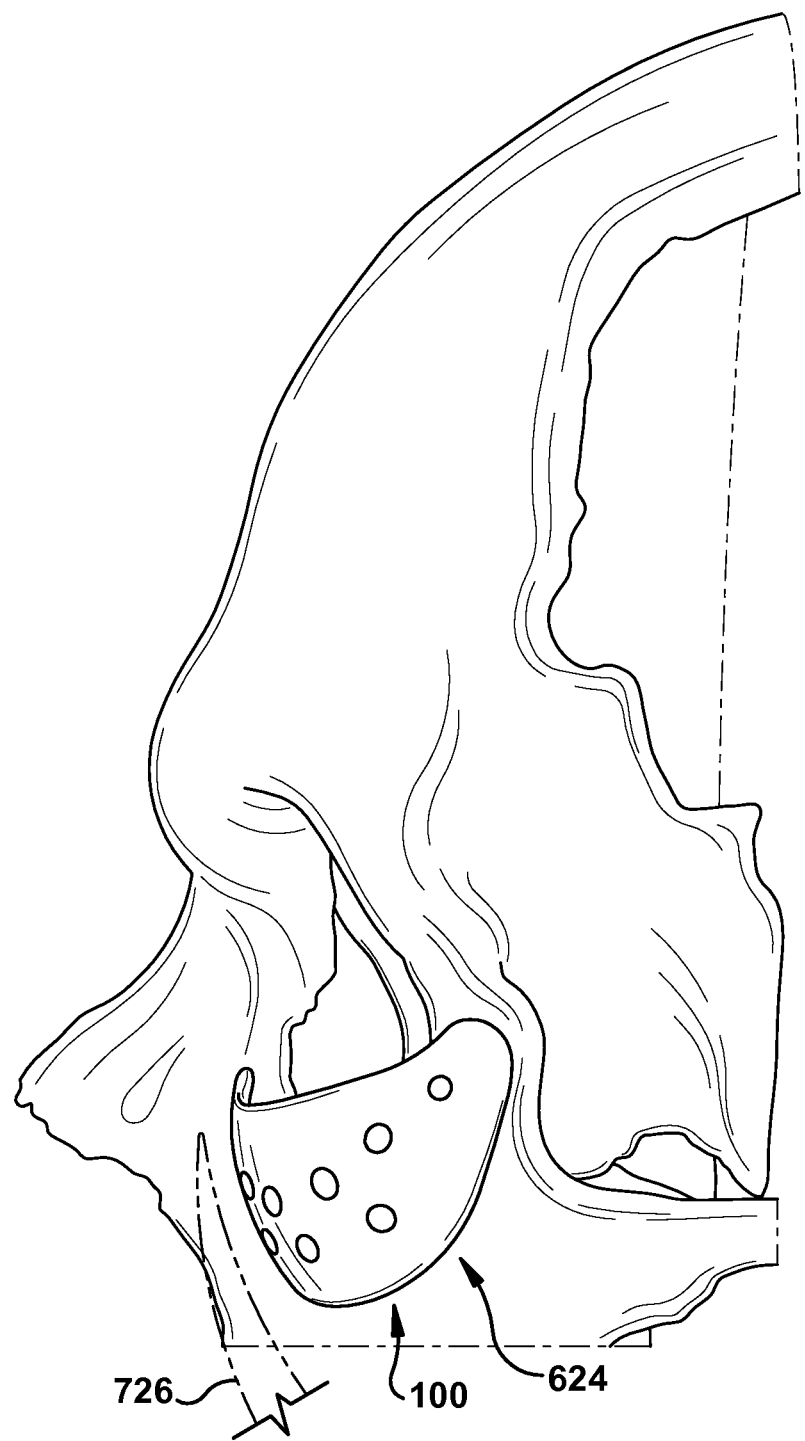
FIG. 8 is a partial lateral view of the construct of FIG. 1 in the example use environment of FIG. 7.

FIGS. 6-8 depict a prosthetic implant 100, shown here as an orbital prosthetic implant, in place upon a patient's facial bony tissue 622. In the implantation process, a predetermined implant site 624 is surgically exposed, in any suitable manner. The prosthetic implant 100 is placed into a predetermined implantation relationship with the implant site 624. For example, and as can be seen in FIGS. 7-8, at least one tab 216 may rest longitudinally on a bony ledge (e.g., the orbital rim) of the patient when the posterior surface 204 is in at least partial contact with a patient's facial bony tissue 622.

Once in place at the implant site 624 as desired, the prosthetic implant 100 is secured in the implantation relationship with the patient's bony tissue. For example, sutures, adhesives, electrocoagulation, screws, other fasteners, or any other attachment means or combinations thereof may be used to actively secure the prosthetic implant 100 into the implantation relationship. As another example, placement of the patient's soft tissue (e.g., the facial soft tissue 726 shown schematically in FIGS. 7-8) into an overlying relationship with the prosthetic implant 100—that is, surgically covering the implant site 624 and prosthetic implant 100 with the soft tissue—could serve to passively secure the prosthetic implant 100 into the implantation relationship, instead of or in addition to active/positive securement. Regardless of the mechanism of initial securement/attachment, however, it is contemplated that ongoing or long-term securement/attachment will occur due to ingrowth of the patient's own native tissue with at least one component (e.g., with porous silicone 208) of the prosthetic implant 100.

Figure 9:
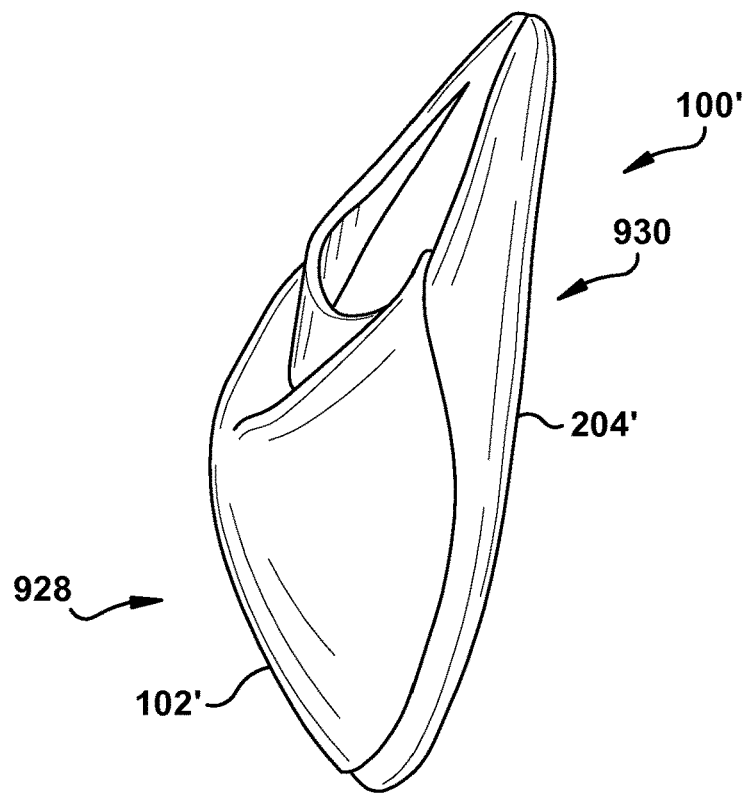
FIG. 9 is a partial lateral view of an example construct according to the present invention.
Figure 10:
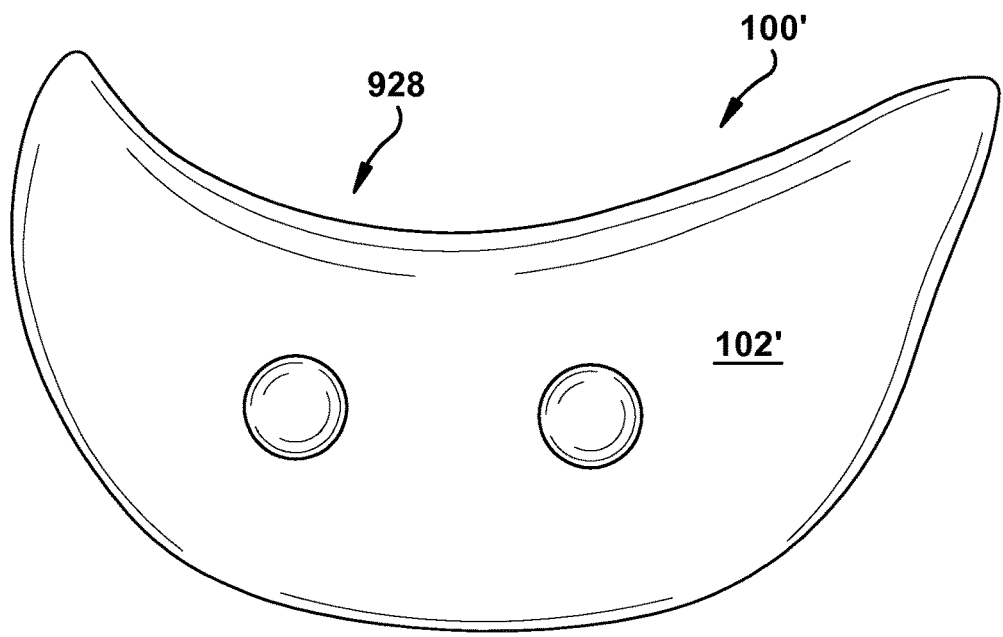
FIG. 10 is a partial posterior view of the construct of FIG. 9.
Figure 11:
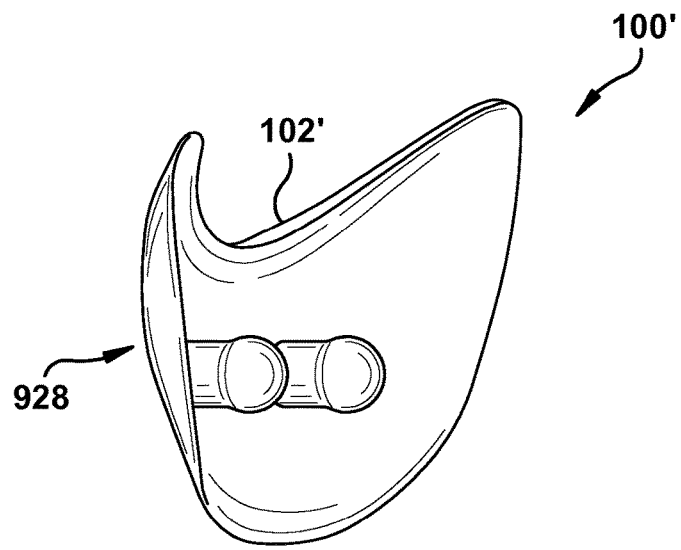
FIG. 11 is a partial lateral perspective view of the construct of FIG. 9.

FIGS. 9-11 illustrate a second construct of the prosthetic implant 100' which may differ from that shown in FIGS. 1-8. Therefore, structures of FIGS. 9-11 that are the same as or similar to those described with reference to FIGS. 1-8 have the same reference numbers with the addition of a "prime" mark. Description of common elements and operation similar to those in the previously described first construct will not be repeated with respect to the second construct.

In FIGS. 9-11, the prosthetic implant 100' is a prosthetic orbital implant which includes anterior and posterior subassemblies 928 and 930, respectively. Through the use of these anterior and posterior subassemblies 928 and 930, the prosthetic implant 100' can be created in a "modular" manner, thereby facilitating different combinations of sizes, shapes, materials, or other physical properties; different manufacturing processes, sources, times, or the like; or otherwise taking advantage of flexibilities and/or economies of scale provided by modular assembly techniques. For example, the anterior and posterior subassemblies 928 and 930 could both be selected from an available range of choices to provide a "semi-custom" prosthetic implant 100' to a patient.

As can be seen in FIGS. 10-11, the anterior subassembly 928 includes at least one peg 1034 which mates with a corresponding hole (not shown) of the posterior subassembly 930 to form the completed prosthetic implant 100'. This mating is optionally accomplished with the assistance of permanent or reversible attachment means (e.g., friction fit, adhesive, welding, or any other suitable attachment means or combination thereof).

Figure 12:
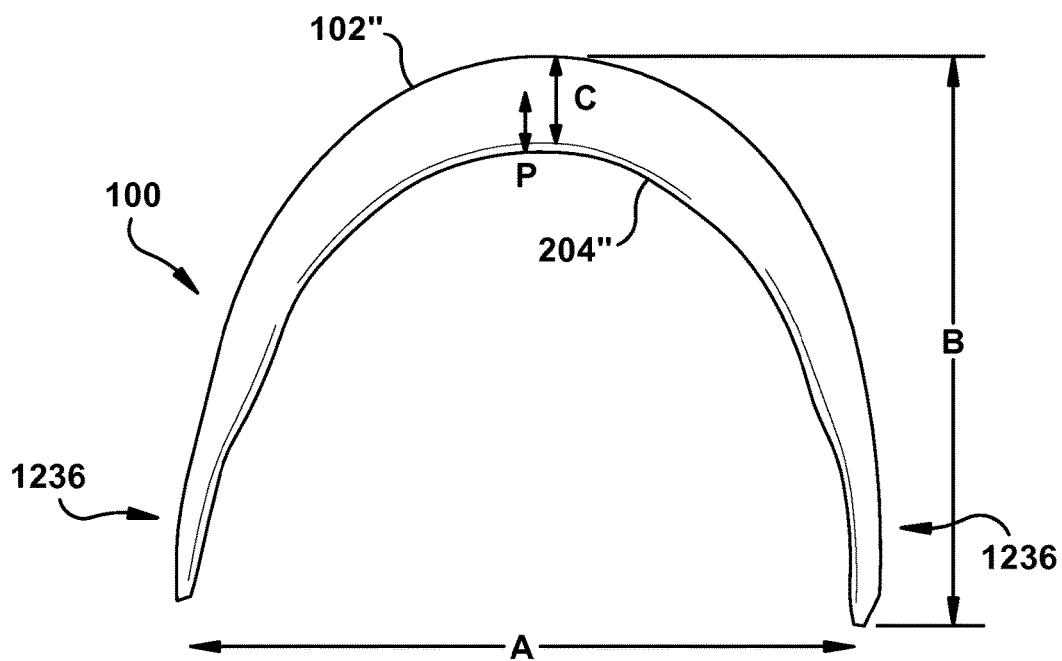
FIG. 12 is a superior view of an example construct according to the present invention.
Figure 13:
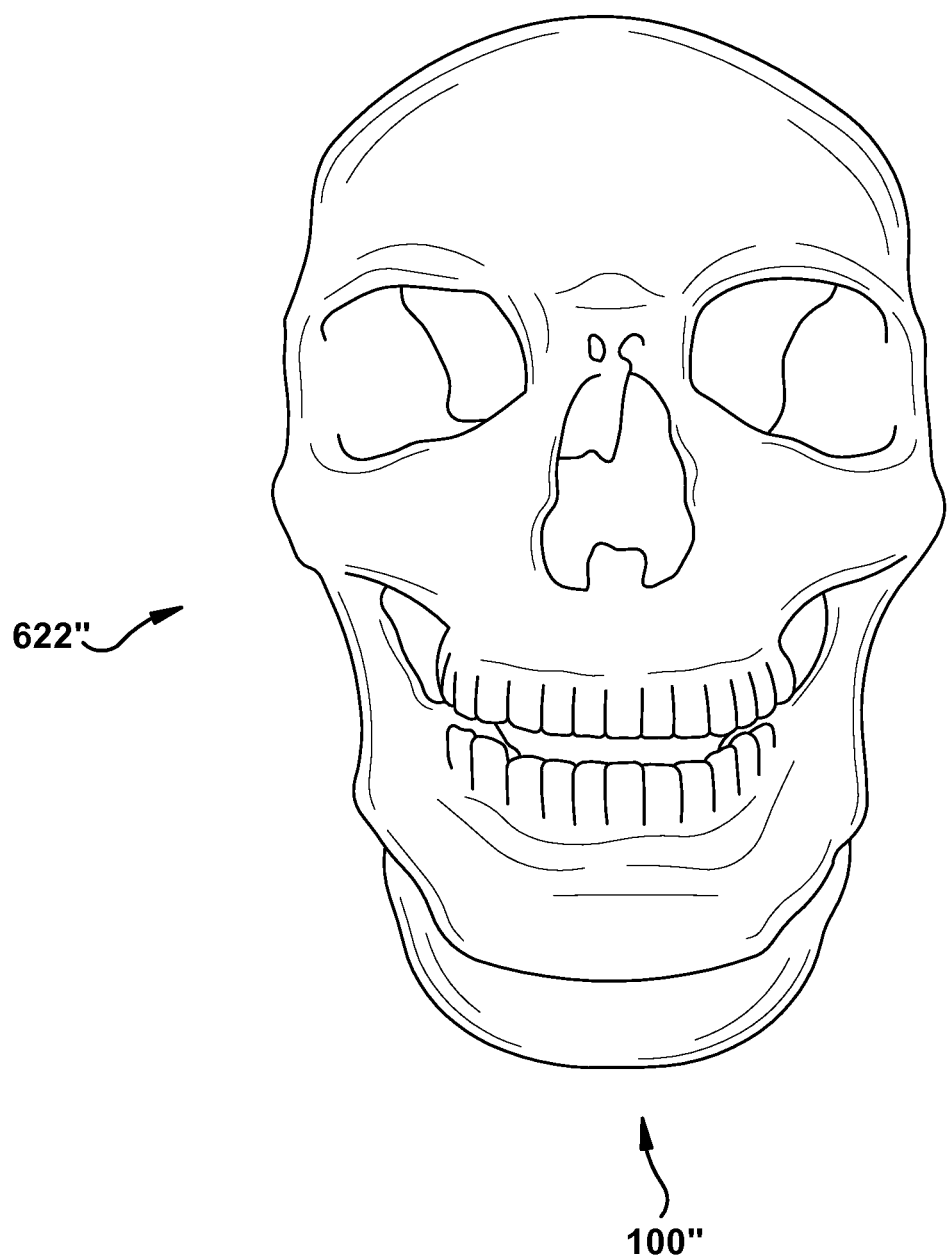
FIG. 13 is a partial anterior view of the construct of FIG. 12 in an example use environment.
Figure 14:
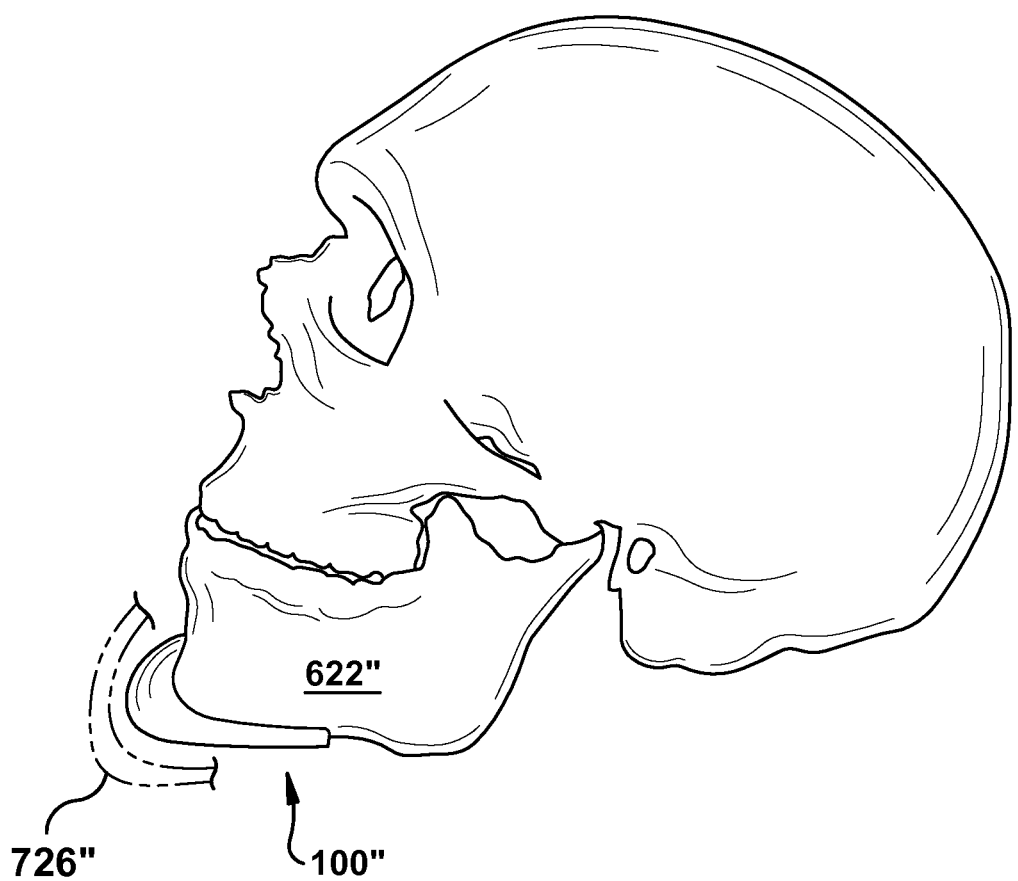
FIG. 14 is a partial lateral view of the construct of FIG. 12 in the example use environment of FIG. 13.

FIGS. 12-14 illustrate a third construct of the prosthetic implant 100" which may differ from those shown in FIGS. 1-11. Therefore, structures of FIGS. 12-14 that are the same as or similar to those described with reference to FIGS. 1-8 have the same reference numbers with the addition of a double "prime" mark. Description of common elements and operation similar to those in the previously described first and second constructs will not be repeated with respect to the third construct.

The prosthetic implant 100" of FIGS. 12-14 is a mandibular, or chin, prosthetic implant. The prosthetic chin implant can help provide cosmetic and/or therapeutic augmentation of the chin. The prosthetic implant 100" shown is configured with anterior and posterior projections, as well as tapered lateral wings 1236 for anatomical fit. As desired, a porous posterior surface 204" may be provided for enhancing bone integration.

TABLE A

Example dimensions for prosthetic chin implant, corresponding to letters in FIG. 12 - "C" is the depth or thickness of the entire implant body 106 between the anterior and posterior surfaces 102" and 204". "P" is the depth or thickness of an example posterior surface 204" which is made from a porous silicone 208" material:
Prototype Dimensions [cm]

| Cat No. | Size | A | B | C | P |
|---------|------|-----|-----|-----|-----|
| Chin | M | 6.5 | 6.0 | 5.6 | 10 |

FIGS. 15A-20 illustrate a fourth construct of the prosthetic implant $100^{iv}$ which may differ from those shown in FIGS. 1-14. Therefore, structures of FIGS. 15A-20 that are the same as or similar to those described with reference to FIGS. 1-14 have the same reference numbers with the addition of a superscript "iv". Description of common elements and operation similar to those in the previously described first through third constructs will not be repeated with respect to the fourth construct.

The prosthetic implant $100^{iv}$ of FIGS. 15A-20 is a malar, or cheek, prosthetic implant. The prosthetic melar implant can help provide cosmetic and/or therapeutic augmentation of the cheek. Malar and/or submalar prosthetic implants $100^{iv}$ can provide contouring of midface and malar and/or skeletal augmentation. The prosthetic implant $100^{iv}$ has an anterior projection 1838 (seen as protruding forward in the orientation of FIG. 18) and a taper 1540 toward the zygomatic arch As desired, a posterior surface $204^{iv}$ including at least some porous silicone $208^{iv}$ may be provided for enhancing bone integration.

TABLE B

Figure 15A:
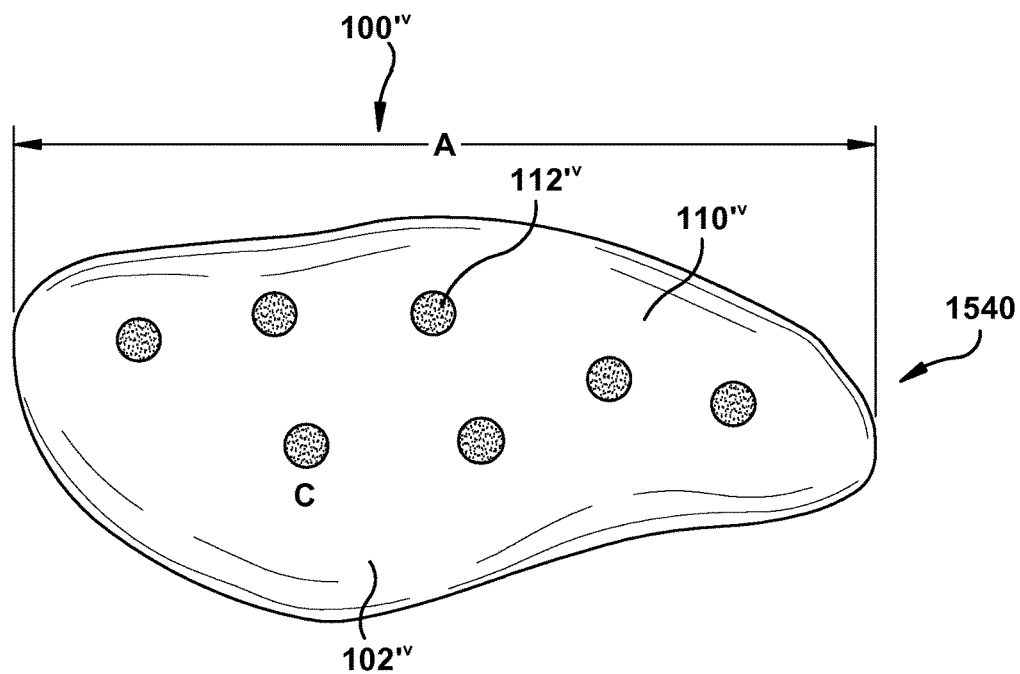
FIG. 15A is an anterior view of an example construct according to the present invention.
Figure 15B:
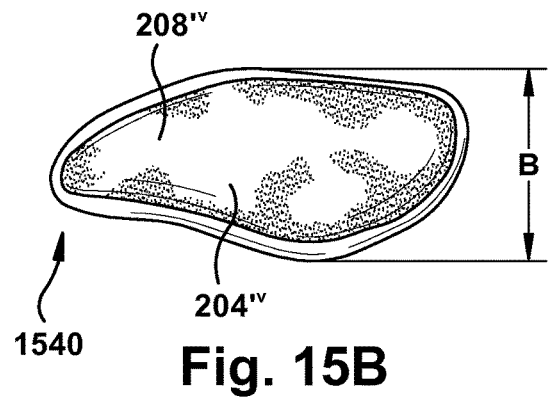
FIG. 15B is a posterior view of the construct of FIG. 15A.
Figure 16:
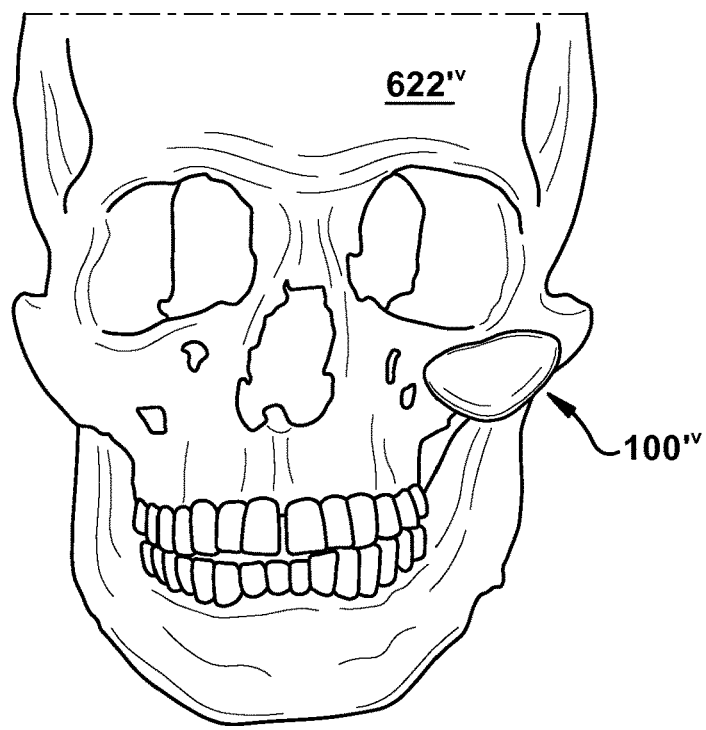
FIG. 16 is a partial anterior view of the construct of FIG. 15A in an example use environment.
Figure 17:
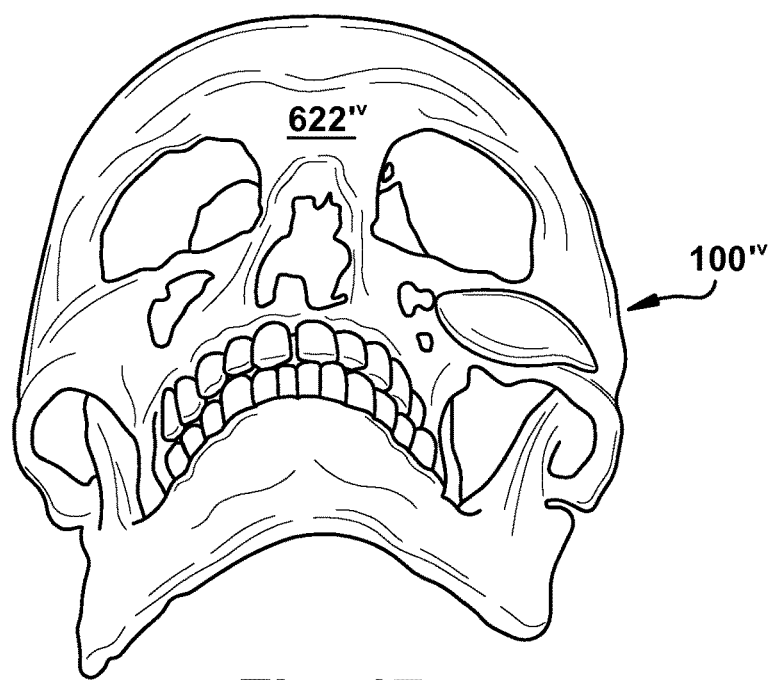
FIG. 17 is a partial inferior view of the construct of FIG. 15A in the example use environment of FIG. 16.
Figure 18:
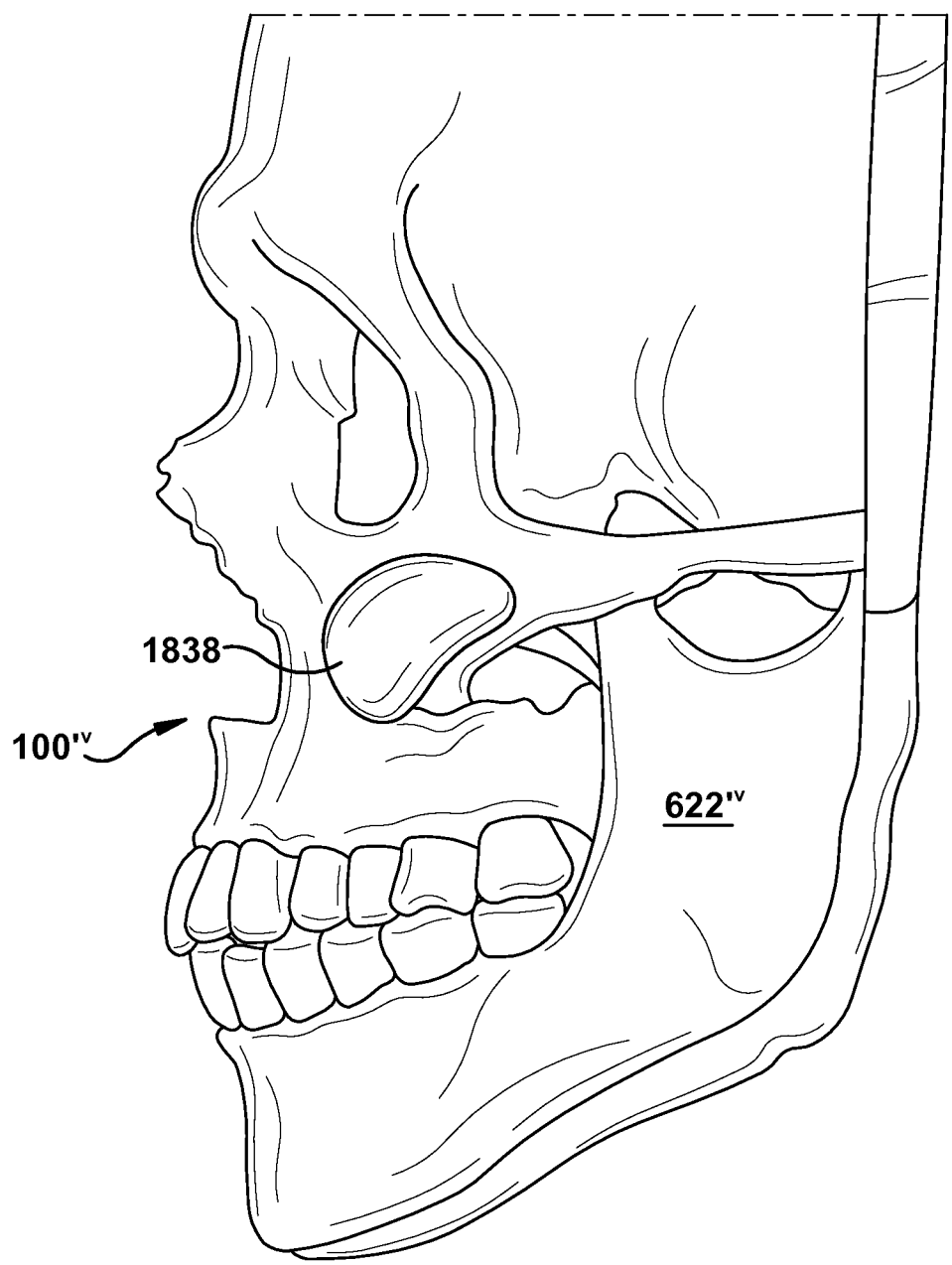
FIG. 18 is a partial lateral view of the construct of FIG. 15A in the example use environment of FIG. 16.

Example dimensions for prosthetic malar implant, corresponding to letters in FIGS. 15A-15B:
Prototype Dimensions [cm]

| Cat No. | Size | A | B | C |
|---------|------|-----|-----|-----|
| Malar | M | 4.1 | 2.0 | .45 |

The prosthetic implant $100^{iv}$ of FIGS. 15A-15B is similar in construction to that of FIGS. 1-2, with an anterior surface $102^{1v}$ which is mostly made of solid silicone $110^{iv}$ but has a plurality of apertures $112^{iv}$ (i.e., a macro-texture) which are each filled with porous silicone $208^{iv}$ (i.e., a micro-texture). The posterior surface $204^{iv}$ of the prosthetic implant $100^{iv}$, shown in FIG. 15B, is almost entirely porous silicone $208^{iv}$ (i.e., a micro-texture), other than a small border near the outer rim of the prosthetic implant $100^{iv}$, where the posterior and anterior surfaces $204^{iv}$ and $102^{iv}$ meet. (This small border may be intentionally provided as a portion of the posterior surface $204^{iv}$, or may be an unintentional artifact of the manufacturing process.)

Figure 19:
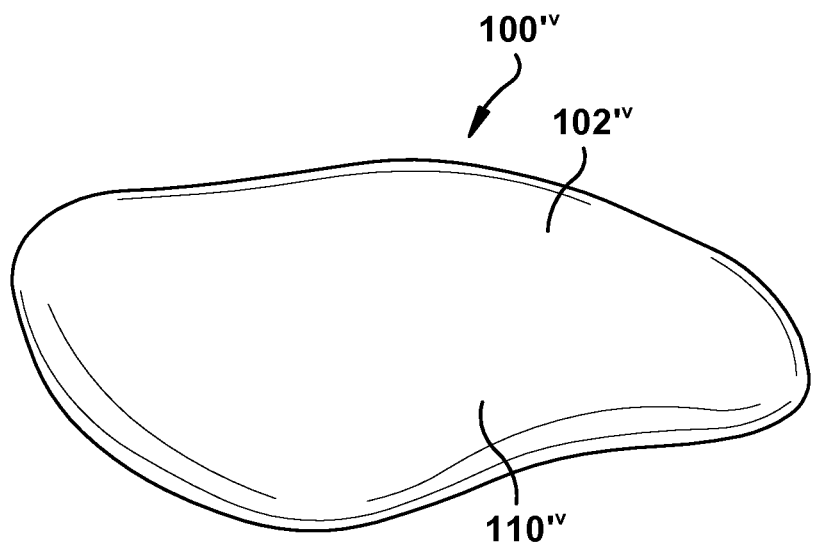
FIG. 19 is an anterior view of an example construct according to the present invention.
Figure 20:
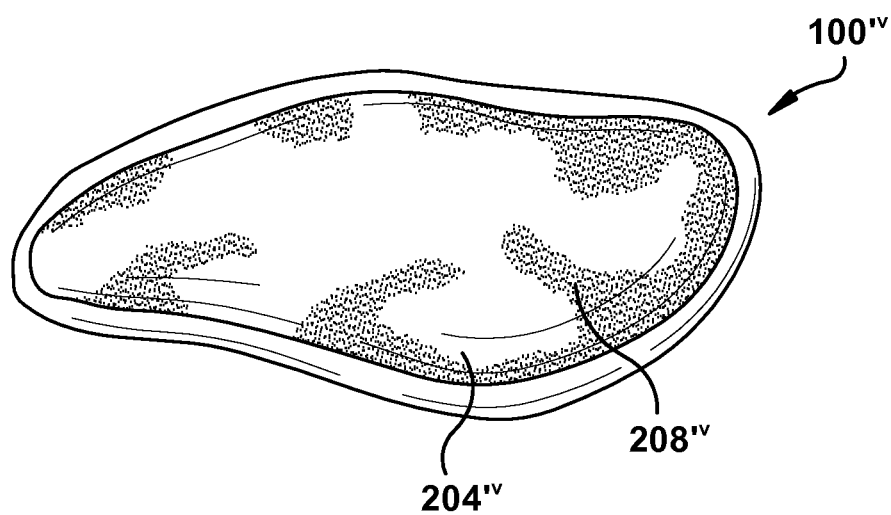
FIG. 20 is a posterior view of the construct of FIG. 19.

In contrast, the prosthetic implant $100^{iv}$ shown in FIGS. 19-20, while also a malar implant, is a differently configured version having an anterior surface $102^{iv}$ that is entirely solid silicone $110^{iv}$ with no apertures $112^{iv}$ and a posterior surface $204^{iv}$ which is entirely, or almost entirely, made of porous silicone $208^{iv}$.

FIGS. 21-25 illustrate a fifth construct of the prosthetic implant $100^v$ which may differ from those shown in FIGS. 1-20. Therefore, structures of FIGS. 21-25 that are the same as or similar to those described with reference to FIGS. 1-20 have the same reference numbers with the addition of a superscript "v". Description of common elements and operation similar to those in the previously described first through fourth constructs will not be repeated with respect to the fifth construct.

The prosthetic implant $100^v$ of FIGS. 21-25 is a nasal prosthetic implant. The prosthetic nasal implant can help provide cosmetic and/or therapeutic augmentation of the nose, such as via dorsum and/or tip augmentation. As with the other implants shown and discussed herein, the nasal implants of these Figures can provide a permanent solution for skeletal augmentation, and/or cosmetic and/or therapeutic reconstruction of the patient's nasal cavity area.

Figure 24:
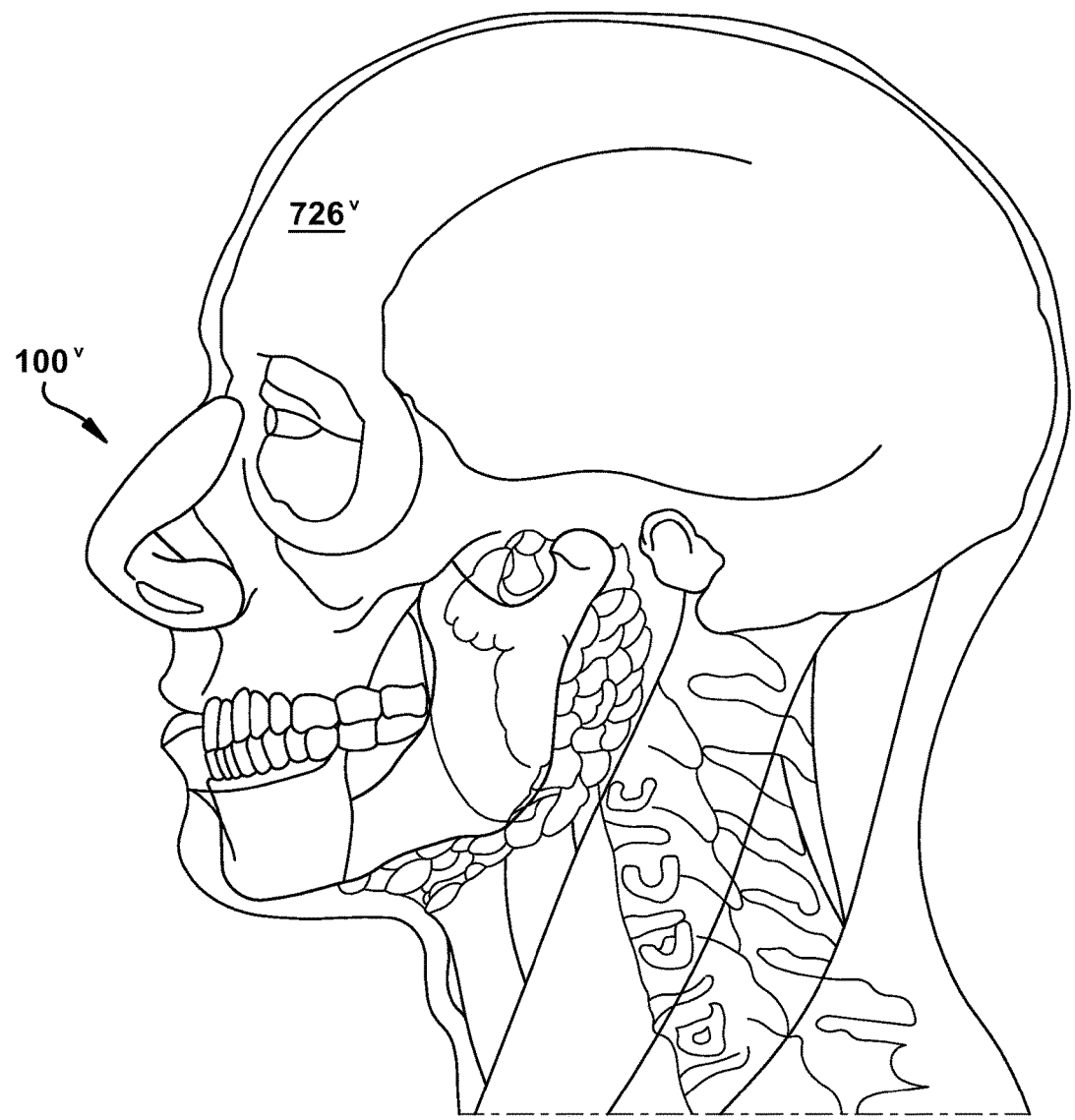
FIG. 24 is a partial lateral view of the construct of FIG. 21 in an example use environment.
Figure 25:
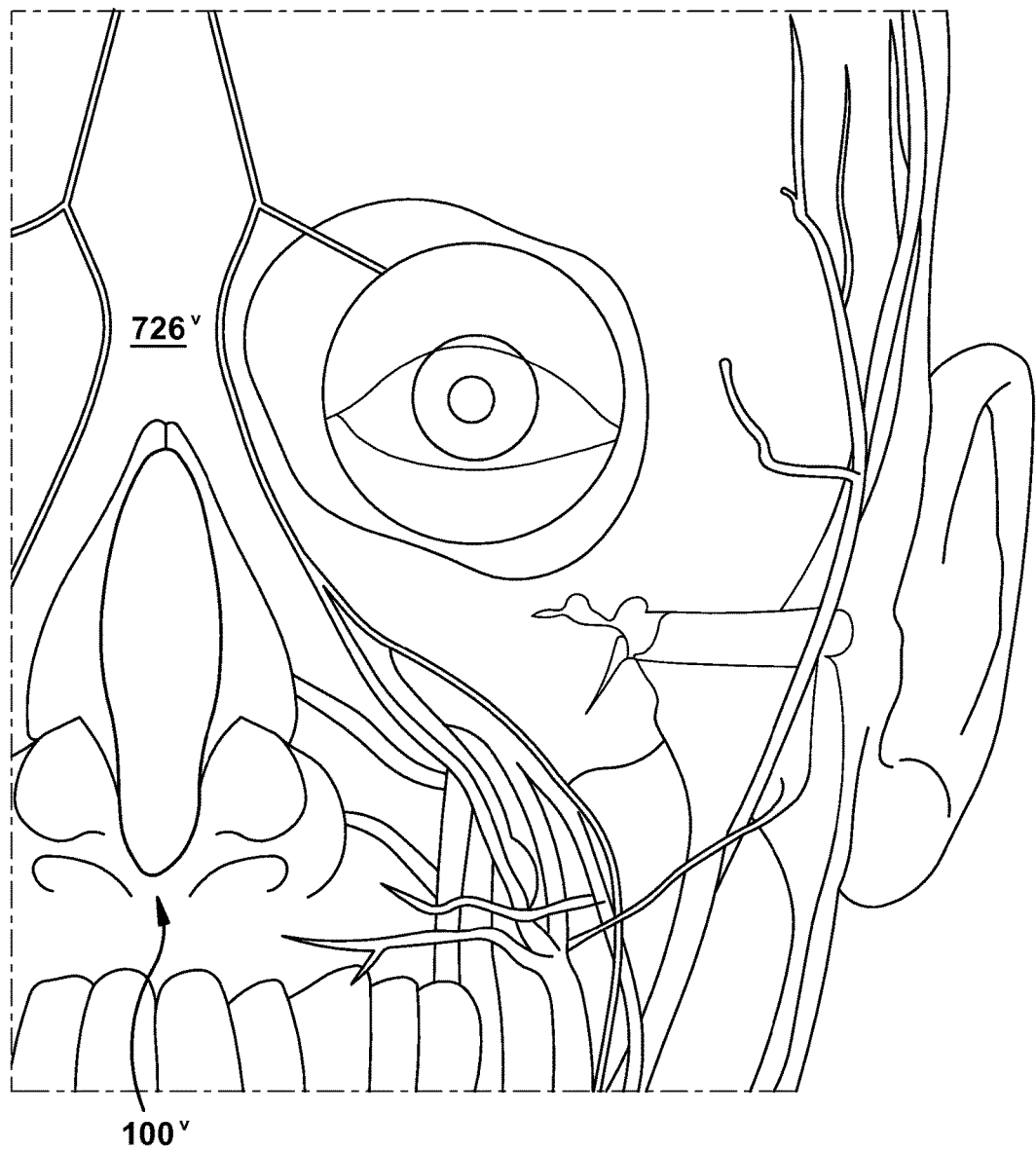
FIG. 25 is a partial anterior view of the construct of FIG. 21 in the example use environment of FIG. 24.

The prosthetic implant $100^v$ has a posterior projection 2142. As desired, a posterior surface $204^v$ including at least some porous silicone $208^v$ may be provided for enhancing bone integration. As can be seen in FIGS. 24-25, the posterior projection 2142 extends from a lower (in the orientation of these Figures) portion of the posterior surface $204^v$. It is noted that, for the nasal prosthetic implant, the posterior projection 2142 may extend back into the nasal cavity to contact the patient's facial bony tissue $622^v$ and help "anchor" the prosthetic implant $100^v$. Other portions of the posterior surface 204$^V$ may come into contact with nasal cartilage and/or other facial soft tissue 726$^V$. The prosthetic implant 100$^V$ may be placed subperiosteally with the posterior projection 2142 tapering off into the glabellar region. Soft tissue on the skin flap may be used to cover the posterior projection 2142.

TABLE C

Figure 21:
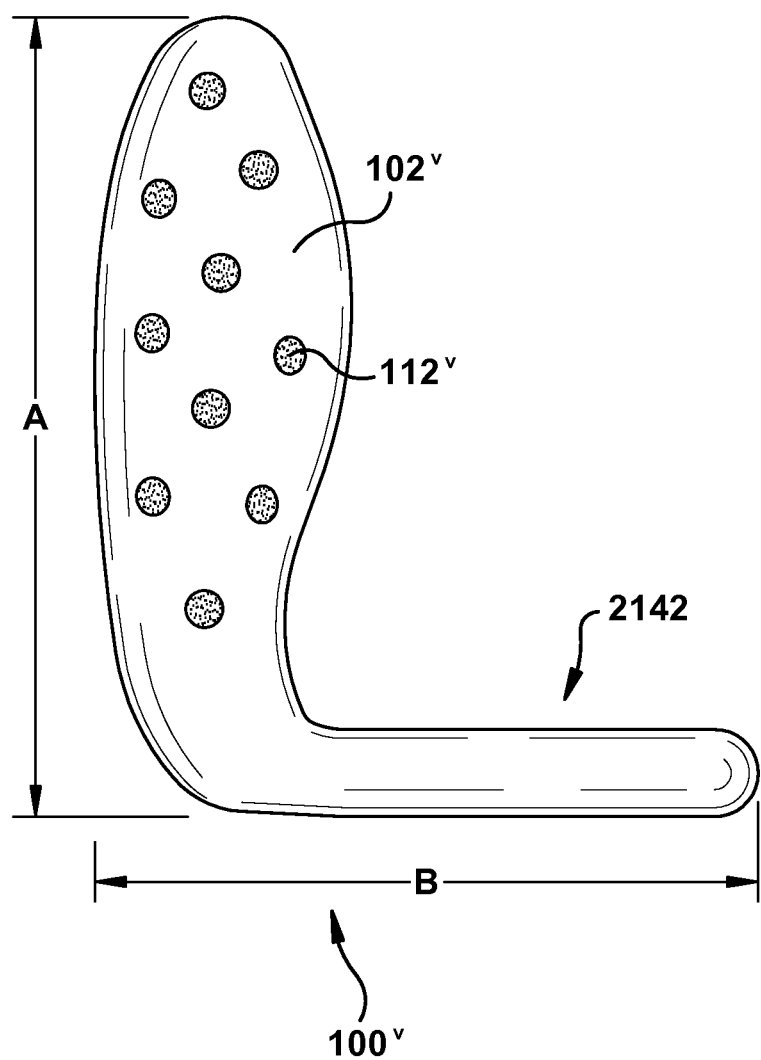
FIG. 21 is a lateral view of an example construct according to the present invention.
Figure 22:
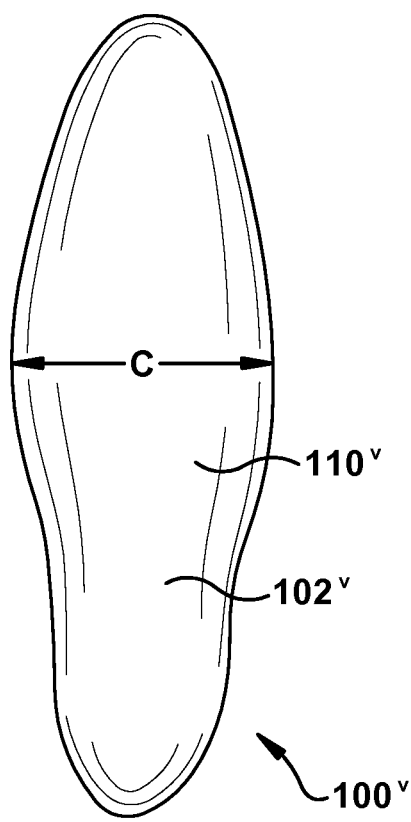
FIG. 22 is a partial anterior view of the construct of FIG. 21.

Example dimensions for silicone nasal implant, corresponding to letters in FIGS. 21-22:
Prototype Dimensions [cm]

| Cat No. | Size | A | B | C |
|---------|------|-----|-----|-----|
| Nasal   | M    | 4.7 | 3.0 | 1.0 |

The prosthetic implant 100$^V$ of FIG. 21 is similar in construction to that of FIGS. 1-2, with an anterior surface 102$^V$ which is mostly made of solid silicone 110$^V$ but has a plurality of apertures 112$^V$ (i.e., a macro-texture) which are each filled with porous silicone 208$^V$ (i.e., a micro-texture). The posterior surface 204$^V$ of the prosthetic implant 100$^V$ may be almost entirely porous silicone 208$^V$ (i.e., a micro-texture), other than a small border near the outer rim of the prosthetic implant 100$^V$, where the posterior and anterior surfaces 204$^V$ and 102$^V$ meet. (This small border may be intentionally provided as a portion of the posterior surface 204$^V$, or may be an unintentional artifact of the manufacturing process.)

Figure 23:
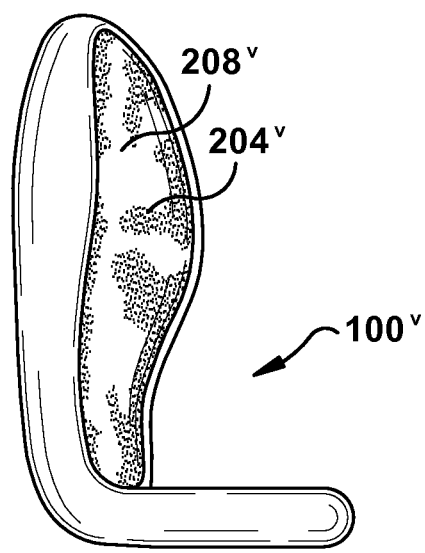
FIG. 23 is a perspective posterior view of the construct of FIG. 21.

In contrast, the prosthetic implant 100$^V$ shown in FIGS. 22-23, while also a nasal implant, is a differently configured version having an anterior surface 102$^V$ that is entirely solid silicone 110$^V$ with no apertures 112$^V$ and a posterior surface 204$^V$ which is entirely, or almost entirely, made of porous silicone 208$^V$.

Regardless of the structure or physical characteristics of a particular construct of a prosthetic implant, however, that prosthetic implant can be implanted in a patient, for temporary (i.e., predetermined to be time-limited) or at least semi-permanent (i.e., not intended to be removed unless such becomes necessary) indwelling. The implantation process described above with reference to FIGS. 6-8, or any other suitable implantation process, could be used and/or adapted as desired by one of ordinary skill in the art for a particular use environment.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. All prosthetic implants discussed herein can be used for permanent cosmetic and/or functional/therapeutic correction of defects such as, but not limited to, bone resorption (e.g., from radiation, age, or any other cause), congenital defect, and/or trauma. The silicone material used as an example material for part or all of the disclosed implants is soft, flexible, easy to trim/alter, and provides a permanent solution for implantation in a patient's body. However, it is contemplated that any desired material or combination of materials could be used with any embodiment of the present invention, although the materials will commonly be biocompatible for implantation. When the silicone is of the porous type (large and/or small scale, as shown herein), the porous silicone may assist with bone/soft tissue integration, decrease bone resorption, and/or enhance integration of the implant with the patient's anatomy. There are a number of possible design options which could be used in various embodiments of the present invention. Instead of, or in addition to, the depicted and described "porous silicone" 208, another solid portion, which may be integrally formed, could be provided; a separate grid or mesh could be provided to any suitable area of the implant; and a texturization process could be applied to at least a portion of the surface of the prosthetic implant 100, which could be a single, unitary piece. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking aiding a user in selecting one component from an array of similar components for a particular use environment. A "predetermined" status may be determined at any time before the structures being manipulated actually reach that status, the "predetermination" being made as late as immediately before the structure achieves the predetermined status. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:
1. A prosthetic implant, comprising:
an anterior surface, configured for at least partial contact with an underside of a patient's facial soft tissue;
a posterior surface, oppositely placed to the anterior surface, the posterior surface being configured for at least partial contact with a patient's facial bony tissue when the anterior surface is in at least partial contact with the patient's facial soft tissue, the anterior and posterior surfaces collectively forming an implant perimeter via the outermost intersection thereof; and
an implant body defined by the anterior and posterior surfaces and extending transversely therebetween, an upper rim being formed by the implant body at a superiormost portion of the implant where the anterior and posterior surfaces intersect, and a portion of the prosthetic implant located directly inferior and adjacent to the upper rim bulges anteriorly to create a protruding dam;

at least one tab protruding transversely from at least a portion of the posterior surface, the at least one tab being configured for engagement with at least a portion of an orbital rim of the patient's facial bony tissue, and the dam extending in a superior-inferior direction, relative to the orbital rim, between the upper rim and the at least one tab, the at least one tab being entirely spaced apart from the implant perimeter; and wherein a selected portion of the posterior surface has a texture that mechanically differs from a texture of a majority of the anterior surface.

2. The prosthetic implant of claim 1, being a prosthetic chin implant.

3. The prosthetic implant of claim 1, being a prosthetic malar implant.

4. The prosthetic implant of claim 1, being a prosthetic orbital implant.

5. The prosthetic implant of claim 1, being a prosthetic nasal implant.

6. The prosthetic implant of claim 1, wherein both the posterior and anterior surfaces are made entirely of porous silicone.

7. The prosthetic implant of claim 1, wherein both the posterior and anterior surfaces are made entirely of solid silicone.

8. The prosthetic implant of claim 1, wherein a selected one of the posterior and anterior surfaces is made entirely of porous silicone and another one of the posterior and anterior surfaces is made entirely of solid silicone.

9. The prosthetic implant of claim 1, including at least one aperture extending entirely through the implant body transversely between the anterior and posterior surfaces for fluid communication therebetween.

10. The prosthetic implant of claim 1, including at least one aperture extending at least partially through the implant body transversely between the anterior and posterior surfaces.

11. The prosthetic implant of claim 10, wherein the at least one aperture contains a material having a texture that mechanically differs from a texture of a majority of a chosen one of the anterior surface and the posterior surface.

12. The prosthetic implant of claim 10, wherein a material contained in the at least one aperture has a texture that is substantially the same as a texture of a majority of the posterior surface.

13. The prosthetic implant of claim 1, wherein the at least one tab includes a plurality of tabs protruding transversely from at least a portion of the posterior surface, the plurality of tabs each being configured for engagement with at least a portion of the patient's facial bony tissue.

14. The prosthetic implant of claim 13, wherein at least one tab of the plurality of tabs rests longitudinally on a bony ledge of the patient when the posterior surface is in at least partial contact with the patient's facial bony tissue.

15. The prosthetic implant of claim 1, wherein the dam is located wholly superior to the at least one tab on the implant body.

* * * * *